United States Patent [19]

Long, Jr.

[11] 4,297,258
[45] Oct. 27, 1981

[54] NON-YELLOWING PAINT FORMULATIONS CONTAINING IODO SUBSTITUTED ALKYNYL URETHANES AS FUNGICIDES

[75] Inventor: William P. Long, Jr., Wilmington, Del.

[73] Assignee: ICI Americas Inc., Wilmington, Del.

[21] Appl. No.: 144,313

[22] Filed: Apr. 28, 1980

[51] Int. Cl.³ .............................................. C08K 5/16
[52] U.S. Cl. ..................... 260/29.6 MN; 106/18.32; 260/29.6 N
[58] Field of Search ................ 260/29.6 N, 29.6 MN; 106/18.32

[56] References Cited

U.S. PATENT DOCUMENTS 3,905,930  9/1975  Dittmar ..................... 260/29.6 MN
3,923,870  12/1975  Singer ............................. 106/18.32

*Primary Examiner*—Paul R. Michl

[57] ABSTRACT

Urethane compounds which are derivatives of 1-iodo substituted low molecular weight alkynes having the formula:

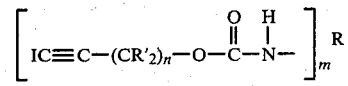

wherein R is a substituted or unsubstituted alkyl, aryl or alkylaryl groups having from one to three linkages corresponding to m, and m and n are whole number integers ranging from 1–3 and may be the same or different, R' is —H, methyl or ethyl group, have increased stability against decomposition to dark colored by-products when employed in aqueous paint systems as emulsified organic solvent solutions.

11 Claims, No Drawings

NON-YELLOWING PAINT FORMULATIONS CONTAINING IODO SUBSTITUTED ALKYNYL URETHANES AS FUNGICIDES

The invention is directed to mildew resistant aqueous paint systems containing a minor amount of 1-iodo-substituted lower alkyne urethane as the active fungicide having the generic formula:

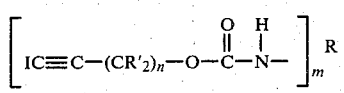

wherein R is selected from the group consisting of substituted or unsubstituted alkyl, aryl, or alkylaryl groups having from one to not more than 20 carbon atoms and having from one to three linkages corresponding to m, and wherein m and n are whole number integers of 1–3 and which may be the same or different and R′ is a H, methyl or alkyl radical which may be the same or different. Such 1-iodo-alkyne urethanes are held in aqueous paint systems as dispersed organic solvent solutions containing selected surfactants and function well as fungicides not only during storage but also after application to surfaces in paint. In particular the invention is directed to stable water emulsifiable concentrates containing the active urethane, organic solvent and surfactant.

Paint systems are liquid, liquefiable, or mastic composition designed for application to a substrate in a thin layer which converts to solid film after application. It usually contains a coloring agent and/or a solid pigment and liquid vehicle. The latter consists of a binder resin which forms a film and a volatile thinner to improve ease of application. Paints of particular interest in this invention are usually characterized as water-based paints wherein water is used as the thinner. A particular type of water-based paint is a heavy bodied thixotropic paint which is free-flowing and easy to manipulate under a brush and sets to a gel within a short time when it is allowed to remain at rest. Because of these qualities a thixotropic paint is less likely to drip from a brush than other types and can be applied in rather thick films without running or sagging.

Some paint binder resins form films by oxidation, polymerization, or cross-linking. Examples are drying oils, epoxies, alkyd resins and polyurethanes. Other binders form films by evaporation of the thinner or by congealing. Examples are polyester, vinyl resins, chlorinated rubber and many polyacrylates and polyethacrylates. Still other binders form a film when particles coalesce from a dispersion of latex or synthetic polymers.

Paints may also contain, as minor constitutents, plastizers, driers, stabilizers, preservatives and anti-foam agents.

Paints usually contain water and solvent insoluble particulate inorganic and organic, natural and synthetic chemical substances which are used to impart color and hiding power to the cured paint film upon application. Primary pigments used to impart hiding power and/or color are titanium dioxide, iron oxide, phthalocyanines, etc. Secondary pigments used as extenders usually contain pigments selected from calcium carbonate, barytes, silica and clay.

Because of their organic component paint systems especially those containing water provide a surface which promotes the growth of fungi such as mildew and mold. These growths take place in stored paint as well as upon the painted surfaces. Fungicides are added to the paint system to control this problem. The above urethanes of 1-iodo substituted lower alkynes which are described in U.S. Pat. No. 3,923,870 are outstanding fungicides for use in paint systems. In certain instances, especially in the case of white or light colored paints, a concomitant discoloration problem associated with the use of the 1-iodo alkyne urethane fungicides arises from either their degradation or unstable by-products occurring with them upon standing in the paint system to form chromophoric materials. This discoloring is not completely understood but it is generally thought to be due to the loss of iodine.

It is generally known that organic epoxides help to stabilize organic iodides by retarding dehydrohalogenation. However, it has been demonstrated that a simple admixture of said 1-iodoalkynyl urethanes (carbamate) and epoxide in paint does not satisfactorily eliminate this discoloration phenomena.

It is the object of this invention to: (1) provide a method for stabilizing monoiodoalkynyl urethane or (carbamate) derivatives used as fungicides in water-base paint systems, (2) provide a stable emulsifiable concentrate of iodo-alkyne urethane fungicides for use in water-base paint systems, and (3) describe water-based paint systems containing iodoalkynyl urethane fungicides which do not discolor severely upon storage and application.

These and other objects of the invention are carried out by the process of first forming an organic solvent solution of the monoiodoalkynyl urethane having the following general formula:

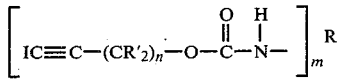

wherein R is selected from the group consisting of substituted or unsubstituted alkyl, aryl or alkylaryl groups having from one to not more than 20 carbon atoms and having from one to three linkages corresponding to m, and m and n are whole number integers of from 1–3 which may be the same or different and R′ is hydrogen, methyl or alkyl radical having up to 6 carbon atoms which may be the same or different in an organic solvent containing a surfactant to form a concentrate, and thereafter dispersing the organic solvent solution in water or a water based paint system such that said iodo alkyne urethane derivative remains in said solvent so that neither partitions into the aqueous phase of the water based paint system.

Typical synthesis of the active component are demonstrated by the following preparations:

In one process, the 1-iodo substituted alkynyl urethane derivatives are prepared by (a) iodinating the appropriate acetylenic alcohol such as, for example, propargyl alcohol (1-propyn-3-OL) to form 1-iodo-1-propyn-3-OL and (b) carrying out a subsequent reaction with an alkyl isocyanate such as n-butylisocyanate or a polyisocyanate such as hexamethylene diisocyanate to form the corresponding urethane derivative.

Extreme caution should be exercised in handling the intermediate of this reaction as well as the final product to prevent exposure in concentrated form to the eyes and skin. Furthermore, these intermediates are highly vesicant and tend to be mildly explosive. No appreciable hazard exists in the dilutions normally employed in paint formulations.

The iodination is conveniently carried out with sodium hypochlorite and an alkali metal iodide. A small molar excess of sodium or potassium iodide, previously dissolved in water, is added to the reaction mixture prior to the addition of hypochlorite. The product is extracted with ether and dried with anhydrous sodium sulfate afterwhich the ether is allowed to evaporate leaving the iodo intermediate product.

The preparation of the urethane derivative may be carried out in solvent such as tetrahydrofuran solution of the iodoalkynol intermediate using a slight stoichiometric excess of isocyanate and small amounts of triethylamine and dibutyltin dilaurate as a catalyst. The reaction mixture is placed in a reaction jar, tightly capped, and heated to 60° C. for 24 hours and thereafter dried to remove solvent or purified by solvent extraction techniques, precipitated and filtered. Suitable product is made by reacting the monoiodoalkynol with a stoichimetric amount of liquid isocyanate at elevated temperatures in a closed system.

For example, methyl, butyl, cyclohexyl, phenyl, octadecyl, t-butyl, allyl, dodecyl, octyl, and hexyl isocyanates as well as hexamethylene diisocyanate have been reacted with 3 hydroxy-1-iodopropyne to make the urethanes. Furthermore, butyl, methyl, and hexyl isocyanates have been reacted with 4 hydroxy-1-iodobutyne to produce urethanes which can be stabilized. Similary, 3,3-dimethyl-3-hydroxy-1-iodopropyne derivatives of urethanes (carbamates) are prepared by reacting the isocyanates of methyl, butyl, cyclohexyl, phenyl, octadecyl, t-butyl, allyl, dodecyl, octyl and hexyl isocyanate.

An alternate process for manufacturing the above-described active involves reacting an alkynol having the formula: $HC\equiv C(CR'_2)_n-OH$ with an isocyanate having the formula $R(NCO)_m$ to give a carbamate of the formula: $[HC\equiv C(CR'_2)_n-OCONH-]_m R$ followed by iodination of the resulting carbamate.

The first stage of this process is carried out by reacting the alkynol with isocyanate in a solvent solution and a catalyst which promotes the formation of the carbamate linkage. The temperature of the reaction mix is moderated by adding one component to the other. Suitable inert solvents are esters such as ethylacetate, butylacetate and 2-ethoxyethylacetate, ketone such as methylethylketone, methylisobutylketone, cyclohexanone and 4-methoxy-4-methyl-pentane-2-one, hydrocarbons such as toluene and xylene, halogenated hard carbons such as trichloroethylene, methylenechloride, 1,1,1-trichloroethane, and tetrachloroethylene and polar aprotic solvents such as dimethylformamide and dimethylacetamide.

The resultant carbamate is isolated from the reaction mixture by conventional means.

In the second stage iodination is carried out in an aqueous media with sodium hypochloride and alkyl metal iodide or sodium hypochloride, an alkyl metal hydroxide and iodine. The product is extracted from the aqueous media with a water immiscible organic solvent for example toluene.

Alternatively, the iodination step may be carried out by treating an aqueous emulsion or dispersion of the alkynol carbamate formed in the first step with an iodination agent. The dispersion or emulsion is preferable formed and stabilized with aid of surfactant so as to maintain the dispersed phase in a finally divided state throughout the reaction.

As suitable surfactants may be used protective colloids such as hydrolyzed or partially hydrolyzed vinylacetates, phase transfer catalysts such as acetyltrimethyl ammonium bromide, and dispersing agents sodium salt of a condensate formaldehyde and naphthalene sulfonic acid and emmulsifying agents such as oxyethylated nonyl phenols.

A monoiodopropynyl N,n-butylcarbamate is commercially available formulation and sold under the trademark Troysan Polyphase Antimildew by Troy Chemical Corp. of Newark, N.J.

Preparation A

A commercially available fungicide (Troysan Polyphase Antimildew) is placed in solution and comprises 40% by weight monoiodo propynyl N,n-butylcarbamate in 60% solvent blend which comprises eight parts propylene glycol and two parts diacetone alcohol.

Preparation B

In a closed container stoichiometric quantities of n-butyl isocyanate is reacted with 3-hydroxy-1-iodopropyne and a catalytic amount of dibutyltin dilaurate and heated to a temperature of 60°–75° C. for a period of 24 hours.

Preparation C

Propargyl alcohol is reacted with a slight excess of n-butyl isocyanate at 20°–25° C. in the presence of dibutyltin dilaurate as catalyst. The resulting propynyl-N-n-butylcarbamate is then iodinated in an aqueous alkaline media with potassium iodide and sodium hypochlorate at a temperature no greater than 10° C. in the presence of a protective colloid (Moviol 3:83). The product which is isolated by filtration followed by washing with water is held as a water-wet paste containing about 35–40% by weight of dry monoiodo propynyl-N-n-butylcarbamate for formulation.

The above-described monoiodoalkynyl urethane (carbamate) derivatives are stabilized by preparing a solution in organic solvents wherein said urethane derivatives are soluble to at least 50 parts per 100 parts solvent by weight. Concentrations of 15–60 percent by weight active are preferred. Aromatic solvents such as xylene, toluene, benzene, mixtures of isomeric trimethyl benzene, ethyl acetate, amyl acetate, butyl acetate, methyl isobutyl ketone, methyl cyclohexanone, monoethylether of ethylene glycol, ethylene glycol monoethylether acetate, ethylene glycol monobutyl ether acetate, and butyl cellosolve acetate are preferred due to their solvency properties for said urethane compounds and their water miscibility. In general aromatic, hydrocarbon, ketone, alcohol, naphthenic, acetate, or ether based substantially water immiscible solvents having water solubility in the range of 0.1–20 parts/100 will suffice. Solvents having a flash point greater than 35° C. are preferred.

To the solvent solution may be added up to 20.0 percent by weight of an organic epoxide stabilizer which is believed to function as a hydrogen iodide acceptor. Satisfactory epoxy based acid scavengers include, but are not limited to, epoxides of vegetable oils/fats, aliphatic resins, cycloaliphatic resins, and aryl resins. Also epoxy derivatives such as propylene oxide, styrene oxide, butylene oxide, and epichlorohydrin can be used. In particular such epoxides include: diglycidylether of bisphenol A; tetraglycidylether of tetraphenylethane; and aliphatic glycidylethers containing primarily n-dodecyl, n-tetradecyl and cycloheyxl alkyl groups such as 3,4 epoxy cyclohexylmethyl-3,4 epoxy cyclohexane carboxylate.

The water immiscible solution must also contain 5–25 percent by weight surfactant which provides for and stabilizes a homogenous dispersion of said water immiscible solution throughout the aqueous phase and the paint. The surfactant can be entirely nonionic, entirely ionic or combinations of nonionic/ionic. Satisfactory surfactants include, but are not limited to, the following: ethoxylated fatty acids, ethoxylated linear fatty alcohols, ethoxylated fatty amines, ethoxylated sorbitan fatty acid esters, ethoxylated alkylphenols, ethoxylated synthetic aliphatic alcohols, akyl/aryl sulfonates, and their metal salts, ethoxylated castor oil, block copolymers of ethylene and propylene oxides, and mixed ethylene oxide (EO) and propylene oxide (PO) alkoxylates of n-butanol. Such suitable surfactant or blends having a hydrophilic/lipophilic balance (HLB)* in the range of 10–17.1.

*Methods for determining the HLB of a substance are set forth in the "The Atlas HLB System" Specialty Chemicals Company of ICI Americas Inc., Wilminton, Del. (1963); and in Petrowski, G. E., and J. R. Vanatta, *J. Am. Chem. Soc.* pp. 284–289, (August, 1973).

Suitable surfactants and surfactant blends are determined by preparing concentrates having 40 parts of the iodoalkynyl urethane active, 35 parts solvent, 15 parts of the surfactant and 10 parts epoxide stabilizer. To test this concentrate, 10 parts are mixed with 100 parts water and shaken to form a milky dispersion. The dispersion is considered preferred if no separation occurs for 7 days upon standing at room temperature.

Water immiscible concentrates of the invention may be stored and added to aqueous paint systems at the time of their manufacture in concentrations of 0.1–4.0 percent by weight based on the weight of the formulated paint.

The following examples are presented to demonstrate, but not limit, operable compositions of the invention. All proportions refer to parts or percent by weight.

EXAMPLE 1

An emulsifiable fungicide concentrate is prepared by dissolving 40 parts of 1-iodopropynyl-N,n-butyl carbamate (Preparation B); 15 parts of an emulsifier blend, and 10 parts of epoxy stabilizer (epoxy resin sold by Union Carbide Inc. under the trademark Bakelite ERL-4221), into 35 parts of aromatic solvent (sold under the trademark Tenneco 100–500 which may be further defined as a mixture of alkylated benzene containing primarily xylenes and trimethyl benzene having the following typical properties: Specific gravity 0.870, flash point 37.5° C., boiling point 145° C.). The epoxy stabilizer, 3,4-epoxy cyclohexyl methyl-3,4-epoxy cyclohexane carboxylate, is cycloaliphatic in nature and has the following typical properties: specific gravity 1.175, boiling point—354° C., viscosity 350–450 cps/25° C. The emulsifier blend consists of 27.4 wt. % calcium dodecylbenzenesulfonate, 11 wt. % polyoxyethylene (POE) (11) nonyphenol, 28.8 wt. % polyoxyethylene (POE) (40) castor oil, 6.0 wt. % polyoxyethylene (POE) (30) nonylphenol, and 26.8 wt. % aromatic solvent diluent.

EXAMPLE 1A

An emulsifiable concentrate is prepared by placing 55.19 parts of an active wet paste described in Preparation C containing 36.9 parts by weight dry solids in a round bottom flask containing 18.61 parts by weight water, 20 parts by weight of methylcyclohexanone, 20 parts by weight of Aromasol H (a mixture of isomeric trimethylbenzene and higher boiling aromatic compounds). The flask is fitted with a water condenser, a thermometer and a stirrer. The contents of the flask are heated to 30° C. with stirring and are stirred at this temperature for 30 minutes. 4.13 Parts by weight of concentrated hydrochloric acid are added and the mixture stirred at 30° C. for a period of 15 minutes. Stirring is then stopped and the mixture transferred to a separating funnel and allowed to stand for one hour. The mixture separates into two layers the lower of which run off into a beaker. The yield of the organic solution is 77.5 parts by weight. 5 Parts by weight of epoxy resin ERL 4221, 20 parts by weight of Synperonic NP 13 (polyoxyethylene(13)nonylphenol) are then added and the concentrate is stirred for an additional five minutes. An emulsifiable concentrate containing 33.8% by weight active is produced.

Emulsifiable concentrates containing 15–60% by weight of the iodine containing carbamate active, 5–25% by weight surfactant, and 20–80% by weight water-immiscible solvent are expected to produce results similar to those obtained in the following examples when applied to paint formulations. In addition the concentrate may contain 0.5–25% by weight stabilizer.

EXAMPLES 2–21

In a similar manner additional examples of the invention were prepared having compositions described in Table 1.

EXAMPLES 22–32

Paint compositions of Table II and a commerical white paint containing no fungicide (duPont Lucite House Paint Batch 10752-174) having no fungicide were dosed with varying amounts of active concentrates prepared according to previous Examples.

Films of 3 mil thickness of each test paint were drawn down on Leneta charts (or other substrates) and allowed to dry. Readings (X, Y and Z coordinates) were made on each chart using a Gardner Reflectometer Model No. XL10-CPM and the Yellowness Index (YI) calculated as follows:

$$(YI) \text{ Yellowness Index} = \frac{100(1.28X - 1.06Z)}{Y}$$

The paints were then held in sealed containers at 60° C. for 7 days in a dark oven to accelerate discoloration. Films of 3 mil thickness of each these heated paints were also prepared and the Yellowness Index determined. The degree of discoloration was reported as $\Delta YI = (YI \ 7th \ day) - (YI \ initial)$. Results for these yellowing tests are listed in Table III.

In order to demonstrate the effect of paint thickness, films having thicknesses of 3,6 and 9 mils were coated on sealed and unsealed Lenata charts. Wet 6 mil coatings were placed over unprimed wood or wood primed with Latex and alkyd paints. duPont acrylic Latex paint number 10752-174 was dosed with 1% Preparation A; 1% Preparation A containing 2.0% of the epoxide stabilizer ERL-4221; and 1% of the concentrate of Ex. 1. The Yellowness Index was determined on the freshly coated substrates and after the painted films were heated at 60° C. for 7 days in a dark oven. Results are tabulated in Table IV.

TABLE I

| | | COMPOSITION OF EMULSIFIABLE CONCENTRATES | | |
|---|---|---|---|---|
| Example No. | 3-iodo propynyl n-butyl carbamate | Water immiscible solvent | Epoxy Stabilizer | Surfactant Blend |
| 2 | 50 parts | 25 parts Tenneco 500/100 | 10 parts Bakelite ERL-4221 | 4.1 parts calcium dodecyl benzene sulfonate<br>1.6 parts POE (11) nonylphenol<br>4.3 parts POE (40) castor oil<br>0.9 parts POE (30) nonylphenol<br>4.1 parts xylene diluent |
| 3 | 55 parts | 20 parts Tenneco 500/100 | 10 parts Bakelite ERL-4221 | Same as example 2 |
| 4 | 60 parts | 15 parts | 10 parts | Same as example 2 |
| 5 | 40 parts | 45 parts Tenneco 500/100 | NONE | Same as example 2 |
| 6 | 40 parts | 40 parts Tenneco 500/100 | 5 parts Bakelite ERL-4221 | Same as example 2 |
| 7 | 40 parts | 35 parts Tenneco 500/100 | 10 parts Epoxide No. 7 | Same as example 2 |
| 8 | 40 parts | 35 parts Tenneco 500/100 | 10 parts Epoxide No. 8 | Same as example 2 |
| 9 | 40 parts | 30 parts Butyl Acetate | 10 parts Bakelite ERL-4221 | 3.26 parts calcium dodecyl benzene sulfonate<br>1.25 parts POE (11) nonylphenol<br>1.2 parts POE (40) castor oil<br>.25 parts POE (30) nonylphenol<br>5.1 parts PO/EO alkoxylates of n-butonol<br>3.94 parts Xylene diluent |
| 10 | 40 parts | 35 parts Ethyl Acetate | 10 parts Bakelite ERL-4221 | 3.36 parts calcium dodecyl benzene sulfonate<br>1.30 parts POE (11) nonylphenol<br>0.60 parts POE (40) castor oil<br>0.12 parts POE (30) nonylphenol<br>5.74 parts PO/EO alkoxylates of n-butanol<br>3.88 parts xylene diluent |
| 11 | 40 parts | 35 parts Cellosolve Acetate | 10 parts Bakelite ERL-4221 | 3.45 parts calcium dodecyl benzene sulfonate<br>6.40 parts PO/EO alkoxylate of n-butanol<br>1.35 parts POE (11) nonylphenol<br>3.80 parts xylene solvent |
| 12 | 40 parts | 45 parts Tenneco 500/100 | 10 parts Bakelite ERL-4221 | 1.36 parts calcium dodecyl benzene sulfonate<br>0.54 parts POE (11) nonylphenol<br>1.44 parts POE (40) castor oil<br>0.30 parts POE (30) nonylphenol<br>1.35 parts xylene diluent |
| 13 | 40 parts | 40 parts Tenneco 500/100 | 10 parts Bakelite ERL-4221 | 2.73 parts calcium dodecyl benzene sulfonate<br>1.00 parts POE (11) nonylphenol<br>2.87 parts POE (40) castor oil<br>0.60 parts POE (30) nonylphenol<br>2.74 parts xylene diluent |
| 14 | 40 parts | 35 parts Tenneco 500/100 | 10 parts Bakelite ERL-4221 | 3.45 parts calcium dodecyl benzene sulfonate<br>1.35 parts POE (11) nonylphenol<br>6.40 parts PO/EO alkoxylate of n-butanol<br>3.8 parts xylene diluent |
| 15 | 40 parts | 35 parts Tenneco 500/100 | 10 parts Bakelite ERL-4221 | 10.5 parts POE (10) nonylphenol<br>3.0 parts calcium dodecyl benzene sulfonate<br>1.5 parts propanol diluent |
| 16 | 40 parts | 35 parts Tenneco 500/100 | 10 parts Bakelite ERL-4221 | 7.5 parts POE (30) nonylphenol<br>5.0 parts calcium dodecyl benzene sulfonate<br>2.5 parts propanol diluent |
| 17 | 40 parts | 35 parts Tenneco 500/100 | 10 parts Bakelite ERL-4221 | 9.0 parts POE (40) castor oil<br>4.0 parts calcium dodecyl benzene sulfonate<br>2.0 parts propanol diluent |
| 18 | 40 parts | 35 parts Tenneco 500/100 | 10 parts Bakelite ERL-4221 | 7.5 parts isopropyl amine dodecyl benzene sulfonate<br>7.5 parts POE (40) castor oil |
| 19 | 40 parts | 35 parts Tenneco 500/100 | 10 parts Bakelite ERL-4221 | 7.5 parts sorbitan mono oleate<br>7.5 parts isopropyl amine dodecyl benzene sulfonate |

TABLE I-continued
COMPOSITION OF EMULSIFIABLE CONCENTRATES

| Example No. | 3-iodo propynyl n-butyl carbamate | Water immiscible solvent | Epoxy Stabilizer | Surfactant Blend |
|---|---|---|---|---|
| 20 | 40 parts | 35 parts Tenneco 500/100 | 10 parts Bakelite ERL-4221 | 7.5 parts POE (5) nonylphenol<br>7.5 parts POE (10) nonylphenol |
| 21 | 40 parts | 35 parts Tenneco 500/100 | 10 parts Bakelite ERL-4221 | 7.5 parts POE (6) tridecyl alcohol<br>7.5 parts POE (15) tridecyl alcohol |

TABLE II
Composition of Latex Paints (% by weight)

| Ingredients | Composition A (100% acrylic) | Composition B (Modified acrylic) | Composition C (Polyvinyl Acetate) |
|---|---|---|---|
| Hydroxyethyl Cellulose | 0.2 | 0.3 | 0.5 |
| Water | 14.4 | 17.3 | 33.1 |
| No salt polymeric carboxylic acid | 1.3 | 1.3 | — |
| Alkyl Aryl polyether | 0.2 | 0.2 | — |
| Ethylene glycol | 2.1 | 2.2 | 1.3 |
| Titanium dioxide | 21.2 | 21.2 | 17.8 |
| Magnesium silicate | 17.3 | 17.3 | 12.3 |
| Acrylic Latex | 29.1 | 33.2 | — |
| Polyvinyl Acetate Emulsion | — | — | 25.0 |
| Tributyl Phosphate | 1.0 | 1.0 | — |
| Propylene glycol | 2.9 | 2.9 | — |
| Ammonium hydroxide | 0.2 | 0.2 | — |
| Defoamer | 0.1 | 0.1 | — |
| Cobalt Naphthenate | — | 0.1 | — |
| Lead Naphthenate | — | 0.1 | — |
| Linseed Oil Alkyd | — | 2.6 | — |
| Silica | — | — | 2.7 |
| Aluminum Silicate | — | — | 4.5 |
| Alkyl Aryl Sulfonate | — | — | 0.3 |
| Ethoxylated Nonyl Phenol | — | — | 0.3 |
| Monoethylether of Diethylene glycol | — | — | 2.2 |

TABLE III
Accelerated Yellowing Tests

| Example No. | Paint | % Concentrate | Degree of Discoloration (ΔYI) |
|---|---|---|---|
| Control A | (du Pont 10752-174) | none | 0.3 |
| Control B | " | 1% Prep. A | 7.4 |
| Control C | (du Pont 10752-174) | 1% Prep. A containing 2% ERL-4221 | 8.7 |
| 22 | (du Pont 10752-174) | 1% of Example 1 | 3.4 |
| 23 | (du Pont 10752-174) | 1% of Example 9 | 2.7 |
| 24 | (du Pont 10752-174) | 1% of Example 10 | 2.2 |
| 25 | (du Pont 10752-174) | 1% of Example 11 | 2.2 |
| 26 | (du Pont 10752-174) | 1% of Example 6 | 0.4 |
| 27 | (du Pont 10752-174) | 1% of Example 5 | 0.7 |
| Control D | Composition A | none | −0.1 |
| Control E | " | 1% of Prep. A | 9.6 |
| Control F | " | 1% of Prep. A contg. 9% of ERL-4221 | 10.0 |
| 28 | " | 1% of Example 1 | 2.4 |
| Control G | Composition A | none | −0.2 |
| Control H | " | 0.5% of Prep. A | 0.7 |
| Control I | " | 1.0% of Prep. A | 2.7 |
| Control J | " | 2.0% of Prep. A | 6.0 |
| 29 | " | 0.5% of Example 1 | 0.3 |
| 30 | " | 1.0% of Example 1 | 0.4 |
| 31 | " | 2.0% of Example 1 | 1.0 |
| 32 | Composition C | 1.0% of Example 1 | 0.5 |

TABLE III-continued
Accelerated Yellowing Tests

| Example No. | Paint | % Concentrate | Degree of Discoloration (ΔYI) |
|---|---|---|---|
| Control K | Composition B | none | −0.3 |
| Control L | " | 1% Prep. A | 15.3 |
| Control N | " | 1% Prep. A Contg. 9% ERL-4221 | 4.2 |
| 33 | " | 1% Example 1 | 0.0 |

TABLE IV
Discoloration vs. Substrate Porosity and Film Thickness

| Mildewcide | Sealed Chart | Unsealed Chart | Latex Primed | Alkyd Primed | Unprimed Wood |
|---|---|---|---|---|---|
|  | (Degree of Discoloration Δ YI) | | | | |
| 3 Mil Wet Film Thickness: | | | | | |
| None (Control) | 0.8 | 0.6 | | | |
| 1% Prep. A | 7.1 | 2.7 | | | |
| 1% Prep. A/2% ERL-4221 | 8.0 | 2.2 | | | |
| 1% Example 1 | 3.4 | 0.9 | | | |
| 6 Mil Wet Film Thickness: | | | | | |
| None (Control)* | 0.5 | 0.5 | 0.5 | 0.2 | 0.0 |
| 1% Prep. A | 8.6 | 2.5 | 7.4 | 10.0 | 2.2 |
| 1% Prep. A/2% ERL-4221 | 9.7 | 2.2 | 4.9 | 9.2 | 3.7 |
| 1% Example 1 | 5.5 | 0.6 | 1.7 | 2.5 | 1.2 |
| 9 Mil Wet Film Thickness: | | | | | |
| None (Control)* | 0.3 | 0.4 | | | |
| 1% Prep. A | 10.0 | 3.5 | | | |
| 1% Prep. A/2% ERL-4221 | 10.3 | 5.0 | | | |
| 1% Example 1 | 4.4 | 1.3 | | | |

*duPont Acrylic Latex Paint No. 10752-174

Coded samples of duPont latex (acrylic) house paint containing the concentrate of the invention were submitted to a commercial testing laboratory for discoloration tests. Films of the paints were prepared and subjected to a proprietary simulated outside exposure procedure. The films were rated (naked eye) as follows:

| Concentrate | Rating |
|---|---|
| None (Control) | No discoloration |
| 1.0% Example 1 | Slight yellowing, such discoloration on houses would require a trained observer to detect. |
| 0.5% Example 1 | Very slight yellowing, such discoloration on houses would be difficult for a trained observer to detect. |

Paint formulations having similar concentrations of unemulsified active with or without stabilizer which were subjected to the same test exposure underwent heavy yellowing.

What is claimed is:

1. A water-dispersible solvent solution concentrate for use as a fungicide in water-base coating systems having an aqueous phase and a binder resin phase which comprises:

(a) an iodo substituted low molecular weight alkyne urethane having the general formula:

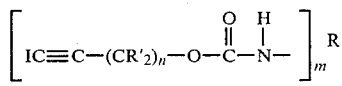

wherein R is selected from the group consisting of substituted or unsubstituted alkyl, aryl or alkylaryl groups having from 1 to 20 carbon atoms and having from one to three linkages corresponding to m, and m and n are whole integers of from 1–3 and may be the same or different, and R' is —H, methyl or alkyl radical which may be the same or different;

(b) a substantially water immiscible organic solvent;

(c) a surfactant selected from the group consisting of ionic and nonionic surfactants having an HLB in the range of 10–17.1 whereby said concentrate can be dispersed such that said iodo compound is not partitioned into said aqueous phase of said water-base coating systems.

2. A composition of claim 1 having 15–60% by weight of an iodo-substituted lower molecular weight alkyne urethane having the general formula:

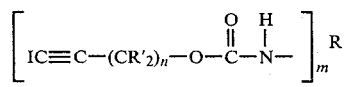

wherein R is an alkyl group having four carbon atoms, m and n are 1, R' is —H.

3. A composition of claim 1 having 25–80% by weight of a water immiscible solvent selected from the group consisting of xylene, toluene, benzene, trimethylbenzene, ethylacetate, amylacetate, butylacetate, methylisobutylketone, methyl cyclohexanane, monoethylether of ethylene glycol and ethylene glycol monoethylether acetate, butyl cellosolve acetate and ethylene glycol monobutylether acetate and organic solvents wherein said iodo compound has a solubility of at least 60 parts per 100 parts solvent by weight.

4. A composition of claim 1 having 0.5–20% by weight of an organic epoxide stabilizer.

5. A composition of claim 4 wherein said epoxide stabilizer is selected from the group consisting of diglycidylether of bisphenol A; tetraglycidyl ether of tetraphenyl ethane; 3,4-epoxy cyclohexylmethyl-3,4 epoxy cyclohexylmethyl carboxylate; and aliphatic glycidyl ethers containing primarily n-dodecyl and n-tetradecyl alkyl groups.

6. A composition of claim 1 having 5–25% by weight of a surfactant selected from ethoxylated fatty acids, ethoxylated linear fatty alcohols, ethoxylated fatty amines, ethoxylated sorbiton fatty acid esters, ethoxylated alkyl phenols, ethoxylated synthetic aliphatic alcohols, alkyl/aryl sulfonates, and metal salts thereof, ethoxylated castor oils, block copolymers of ethylene and propylene oxides, and mixed ethylene oxide and propylene oxides alkoxylates of n-butanol.

7. A composition of claim 6 wherein said surfactants are selected from the group consisting of calcium dodecyl benzene sulfonate, polyoxyethylene (11) nonylphenol, polyoxyethylene (40) castor oil, polyoxyethylene (30) nonylphenol, isopropylamine dodecylbenzene sulfonate, sorbitan monooleate, polyoxyethylene (5) nonylphenol, polyoxyethylene (10) nonylphenol, polyoxyethylene (6) tridecyl alcohol, and polyoxyethylene (15) tridecyl alcohol.

8. A composition of claim 7 wherein said surfactant is a blend consisting essentially of calcium dodecylbenzene sulfonate, polyoxyethylene (11) nonylphenol, polyoxyethylene (40) castor oil and polyoxyethylene (30) nonylphenol.

9. A composition of claim 1 further comprising up to 90% by weight water.

10. A non-yellowing coating system including from 0.1–4% by weight of a composition of claim 1.

11. A process for the manufacture of a composition of claim 10 which comprises first preparing an aqueous composition of claim 9 and thereafter incorporating said composition of claim 9 into a water-base resin coating system.

* * * * *